(12) United States Patent
Grewe

(10) Patent No.: US 8,118,853 B2
(45) Date of Patent: Feb. 21, 2012

(54) PROSTHESIS DELIVERY AND DEPLOYMENT DEVICE

(75) Inventor: David D. Grewe, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1129 days.

(21) Appl. No.: 11/764,969

(22) Filed: Jun. 19, 2007

(65) Prior Publication Data

US 2007/0293934 A1 Dec. 20, 2007

Related U.S. Application Data

(60) Provisional application No. 60/814,760, filed on Jun. 19, 2006.

(51) Int. Cl.
*A61F 2/06* (2006.01)
(52) U.S. Cl. ...................................... 623/1.11
(58) Field of Classification Search ............... 623/1.11, 623/1.12, 1.23; 606/108, 194, 195; 604/216
See application file for complete search history.

(56) References Cited

U.S. PATENT DOCUMENTS

| | | | |
|---|---|---|---|
| 4,562,596 A | 1/1986 | Kornberg | |
| 4,665,918 A | 5/1987 | Garza et al. | |
| 4,921,484 A | 5/1990 | Hillstead | |
| 5,078,720 A | 1/1992 | Burton et al. | |
| 5,092,877 A | 3/1992 | Pinchuk | |
| 5,201,757 A | 4/1993 | Heyn et al. | |
| 5,380,304 A | 1/1995 | Parker | |
| 5,415,664 A | 5/1995 | Pinchuk | |
| 5,445,646 A | 8/1995 | Euteneuer et al. | |
| 5,534,007 A | 7/1996 | St. Germain et al. | |
| 5,626,603 A | 5/1997 | Venturelli et al. | |
| 5,690,644 A | 11/1997 | Yurek et al. | |
| 5,817,101 A | 10/1998 | Fiedler | |
| 5,928,197 A * | 7/1999 | Niehoff | 604/155 |
| 5,968,052 A * | 10/1999 | Sullivan et al. | 623/1.11 |
| 6,056,759 A | 5/2000 | Fiedler | |
| 6,113,608 A * | 9/2000 | Monroe et al. | 623/1.11 |
| 6,152,931 A * | 11/2000 | Nadal et al. | 606/108 |
| 6,206,888 B1 | 3/2001 | Bicek et al. | |
| 6,254,611 B1 | 7/2001 | Vrba | |
| 6,514,261 B1 | 2/2003 | Randall et al. | |
| 6,579,297 B2 | 6/2003 | Bicek et al. | |
| 6,605,109 B2 | 8/2003 | Fiedler | |
| 6,626,934 B2 | 9/2003 | Blaeser et al. | |
| 6,669,716 B1 | 12/2003 | Gilson et al. | |
| 6,849,084 B2 | 2/2005 | Rabkin et al. | |
| 6,858,034 B1 | 2/2005 | Hijlkema et al. | |

(Continued)

FOREIGN PATENT DOCUMENTS

EP 0696447 B1 2/1996

(Continued)

*Primary Examiner* — Leslie Deak
*Assistant Examiner* — Katherine Dowe
(74) *Attorney, Agent, or Firm* — Brinks Hofer Gilson & Lione

(57) ABSTRACT

A system for delivering and deploying an expandable endoluminal prosthesis comprises a delivery catheter and a sheath. The delivery catheter has a proximal end and a distal end and is slidably disposed within a lumen of the sheath. An operating mechanism comprises a contractible air vessel that couples the sheath and the delivery catheter so that contraction of the air vessel causes the sheath to retract proximally over the delivery catheter. Additional aspects of the invention include a method of deploying an expandable endoluminal prosthesis.

20 Claims, 9 Drawing Sheets

U.S. PATENT DOCUMENTS

| | | |
|---|---|---|
| 6,911,039 B2 | 6/2005 | Shiu et al. |
| 7,122,050 B2 | 10/2006 | Randall et al. |
| 2001/0012944 A1 | 8/2001 | Bicek et al. |
| 2001/0034514 A1 | 10/2001 | Parker |
| 2002/0045929 A1 | 4/2002 | Diaz |
| 2003/0109886 A1 | 6/2003 | Keegan et al. |
| 2004/0098079 A1 | 5/2004 | Hartley et al. |
| 2004/0106974 A1 | 6/2004 | Greenberg et al. |
| 2004/0127912 A1 | 7/2004 | Rabkin et al. |
| 2004/0133264 A1 | 7/2004 | Moore |
| 2005/0060018 A1 | 3/2005 | Dittman |
| 2005/0085890 A1 | 4/2005 | Rasmussen et al. |
| 2005/0090887 A1 | 4/2005 | Pryor |
| 2005/0273151 A1 | 12/2005 | Fulkerson et al. |
| 2006/0282150 A1* | 12/2006 | Olson et al. .............. 623/1.11 |
| 2006/0282152 A1* | 12/2006 | Beyerlein et al. .......... 623/1.11 |
| 2007/0060999 A1 | 3/2007 | Randall et al. |
| 2007/0233222 A1* | 10/2007 | Roeder et al. ............ 623/1.11 |

FOREIGN PATENT DOCUMENTS

| | | |
|---|---|---|
| WO | WO 95/11055 A1 | 4/1995 |
| WO | WO 98/53761 A1 | 12/1998 |

\* cited by examiner

PROSTHESIS DELIVERY AND DEPLOYMENT DEVICE

RELATED APPLICATIONS

This application claims the benefit of the filing date under 35 U.S.C. §119(e) of U.S. Provisional Patent Application Ser. No. 60/814,760, filed Jun. 19, 2006, which is incorporated herein by reference.

BACKGROUND OF THE INVENTION

1. Field of the Invention

This invention relates to a medical device and, in particular, to a delivery and deployment device for an expandable prosthesis and a method of deploying a prosthesis in a body lumen.

2. Description of Related Art

Endoluminal prostheses, such as stents and stent grafts, are used for treating damaged or diseased body lumens such as the esophagus, bile duct, and blood vessels. For example, endoluminal prostheses may be used for repairing diseased aortas including abdominal aortic aneurysms and thoracic aortic aneurysms. Such a prosthesis is placed inside the body lumen and provides some or all of the functionality of the original, healthy vessel.

The deployment of endoluminal prostheses into the lumen of a patient from a remote location by the use of a catheter delivery and deployment device is well known in the art. For example, PCT Patent Publication Number WO 98/53761 entitled "A Prosthesis and a Method and Means of Deploying a Prosthesis," which is incorporated herein by reference, proposes a deployment system for an endoluminal prosthesis. The prosthesis is radially compressed onto a delivery catheter and is covered by an outer sheath. To deploy the system, the operator slides the outer sheath over the delivery catheter, thereby exposing the prosthesis. The prosthesis expands outwardly upon removal of the sheath. Such a delivery and deployment device has been referred to as a "push-pull" system because as the operator pulls the sheath proximally in relation to the delivery catheter, the delivery catheter pushes the prosthesis out of the sheath.

Devices, such as the ones described in WO 98/53761 have several advantages. To deploy the prosthesis, the operator can directly manipulate the sheath and the delivery catheter. This provides the operator with a relatively high degree of control during the procedure. Further, such devices may be compact and may have a relatively uniform, low-diameter radial profile, allowing for atraumatic access and delivery. In order to provide a low-diameter profile, the delivery catheter, the sheath, and the prosthesis are often very tightly interconnected. As a result, manual retraction of the sheath may be challenging. An exemplary delivery and deployment device may require as much as 100 Newtons or approximately 22.5 pounds of force to deploy. Such resistance can easily tire an operator and accordingly is highly undesirable.

SUMMARY

According to an aspect of the invention, a system for delivering and deploying an expandable endoluminal prosthesis is provided and comprises an elongate sheath and a delivery catheter. The sheath has a proximal end, a distal end, and an inner lumen. The delivery catheter has a proximal end and a distal end and is slidably disposed within the sheath lumen. An operating mechanism may be provided for retracting the sheath over the delivery catheter. The operating mechanism comprises a contractible air vessel having an expanded length and a contracted length. The air vessel couples the sheath and the delivery catheter so that pneumatic contraction of the air vessel causes the sheath to retract proximally over the delivery catheter.

According to an aspect of the invention, the air vessel may comprise a resilient tubular member having a proximal end, a distal end, and a lumen disposed therebetween. The tubular member may be radially disposed about the sheath and the delivery catheter, where the distal end of the tubular member sealingly engages the sheath and the proximal end of the tubular member sealingly engages the delivery catheter. The tubular member, the sheath, and the delivery catheter define an annular air chamber therebetween.

According to another aspect of the invention, the air vessel may comprise a tubular bellows. The bellows may be constructed of any suitable material, including metal, rubber, thermoplastic elastomer, polyolefin, or a fluoropolymer material such as polytetrafluoroethylene or fluoroethylene-propylene. The bellows couples the sheath and the delivery catheter such that contraction of the bellows causes the sheath to retract proximally over the delivery catheter.

The operating mechanism may include an air port that is configured to provide pneumatic communication between the air vessel and a pressure source. The pressure source may be a sub-atmospheric pressure source, or a vacuum. The operating mechanism may further comprise an actuation switch that is configured to selectively halt contraction of the air vessel by effecting pneumatic communication between the pressure source and the air chamber. Still further, the operating mechanism may comprise a check valve for preventing expansion of the air vessel.

According to another aspect of the invention, the system may comprise a mechanical conversion mechanism for converting air vessel contraction into sheath retraction. The conversion mechanism may comprise a linear gear that is configured to mechanically increase or to decrease sheath retraction in relation to vessel contraction. Accordingly, the conversion mechanism may cause the ratio between sheath retraction and vessel contraction to be less than or greater than 1.

According to another aspect of the invention, a pneumatic operating mechanism may be provided for an endoluminal prosthesis delivery and deployment device having a sheath and a delivery catheter slidingly disposed within a lumen of the sheath. The operating mechanism may comprise a contractible air vessel having a proximal end, a distal end, an expanded length, and a contracted length. The proximal end of the air vessel is engageable with the delivery catheter and the distal end of the air vessel is engageable with the sheath so that contraction of the air vessel causes the sheath to retract proximally over the delivery catheter. The air vessel may comprise various features, for example, a tubular bellows, a check valve, an air port, and/or a mechanical conversion mechanism as described above.

According to yet another aspect of the invention, a method of deploying an expandable endoluminal prosthesis is disclosed. A prosthesis delivery and deployment system is provided and comprises an elongate sheath and a delivery catheter slidably disposed within a lumen of the sheath. An operating mechanism is provided and comprises a contractible air vessel having an expanded length and a contracted length. The air vessel couples the sheath and the delivery catheter. The method may further comprise the step of pneumatically contracting the air vessel to cause the sheath to retract over the delivery catheter. The contracting step may comprise applying vacuum pressure to the air chamber.

DETAILED DESCRIPTION OF PREFERRED EMBODIMENTS

Throughout the specification, the terms "distal" and "distally" shall denote a position, direction, or orientation that is generally toward the patient. Accordingly, the terms "proximal" and "proximally" shall denote a position, direction, or orientation that is generally away from the patient.

Figure 1:
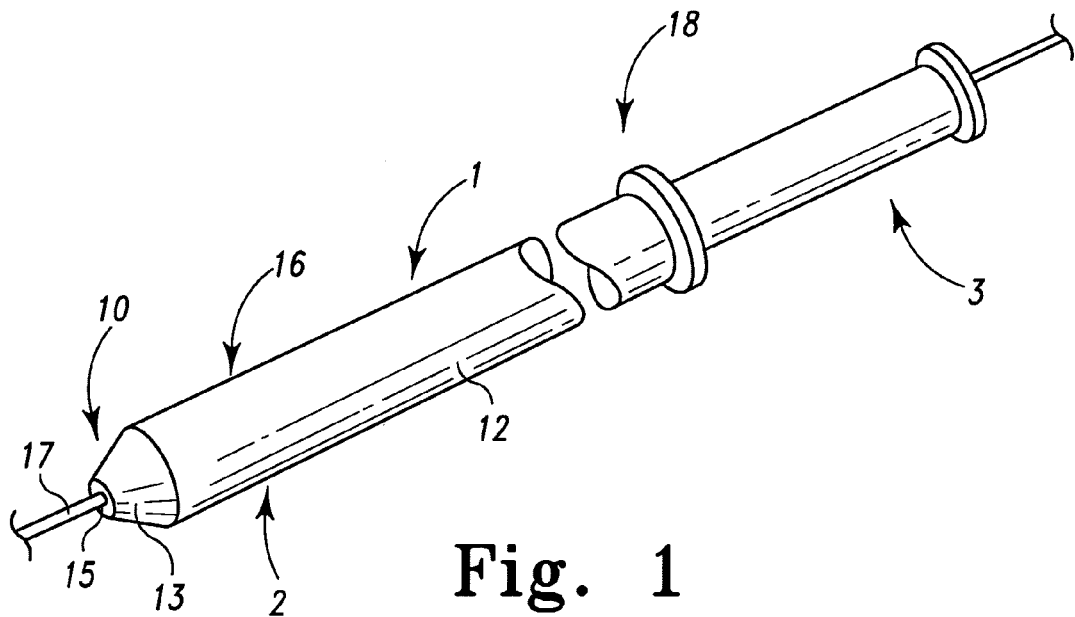
FIG. 1 is a perspective view of a delivery and deployment device according to an aspect of the present invention.
Figure 2:
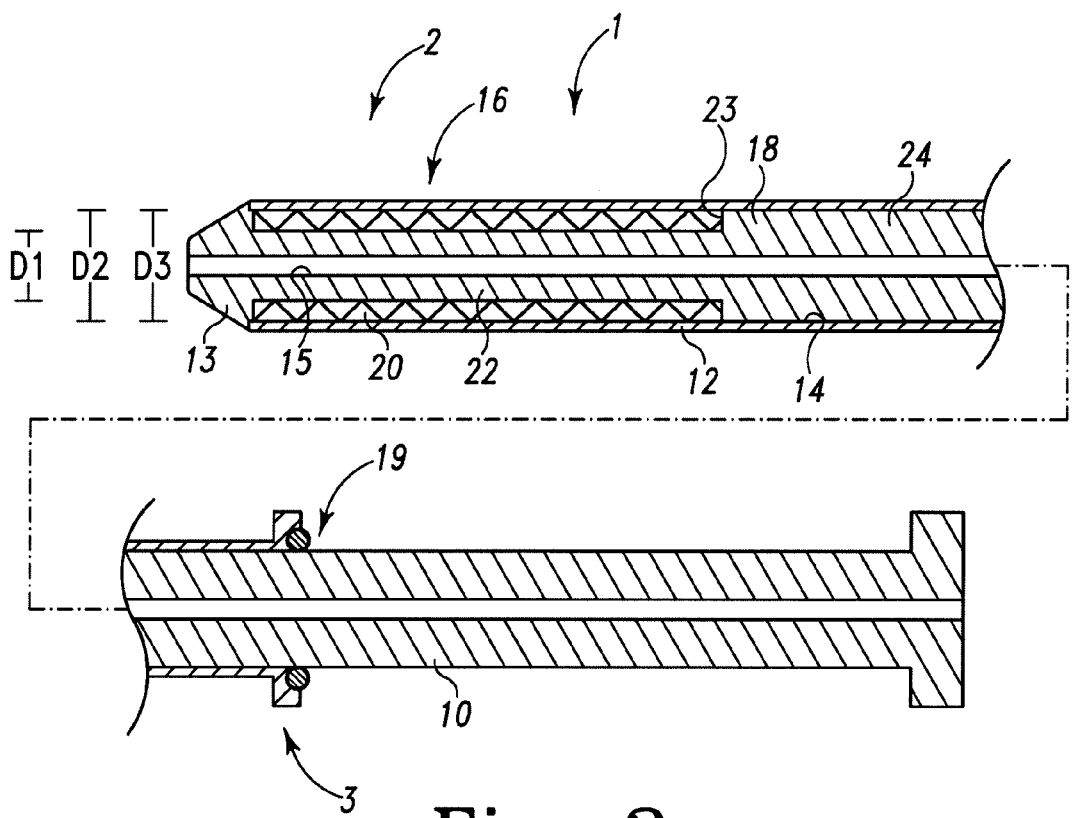
FIG. 2 is a cross-sectional view of the device of FIG. 1.
Figure 3:
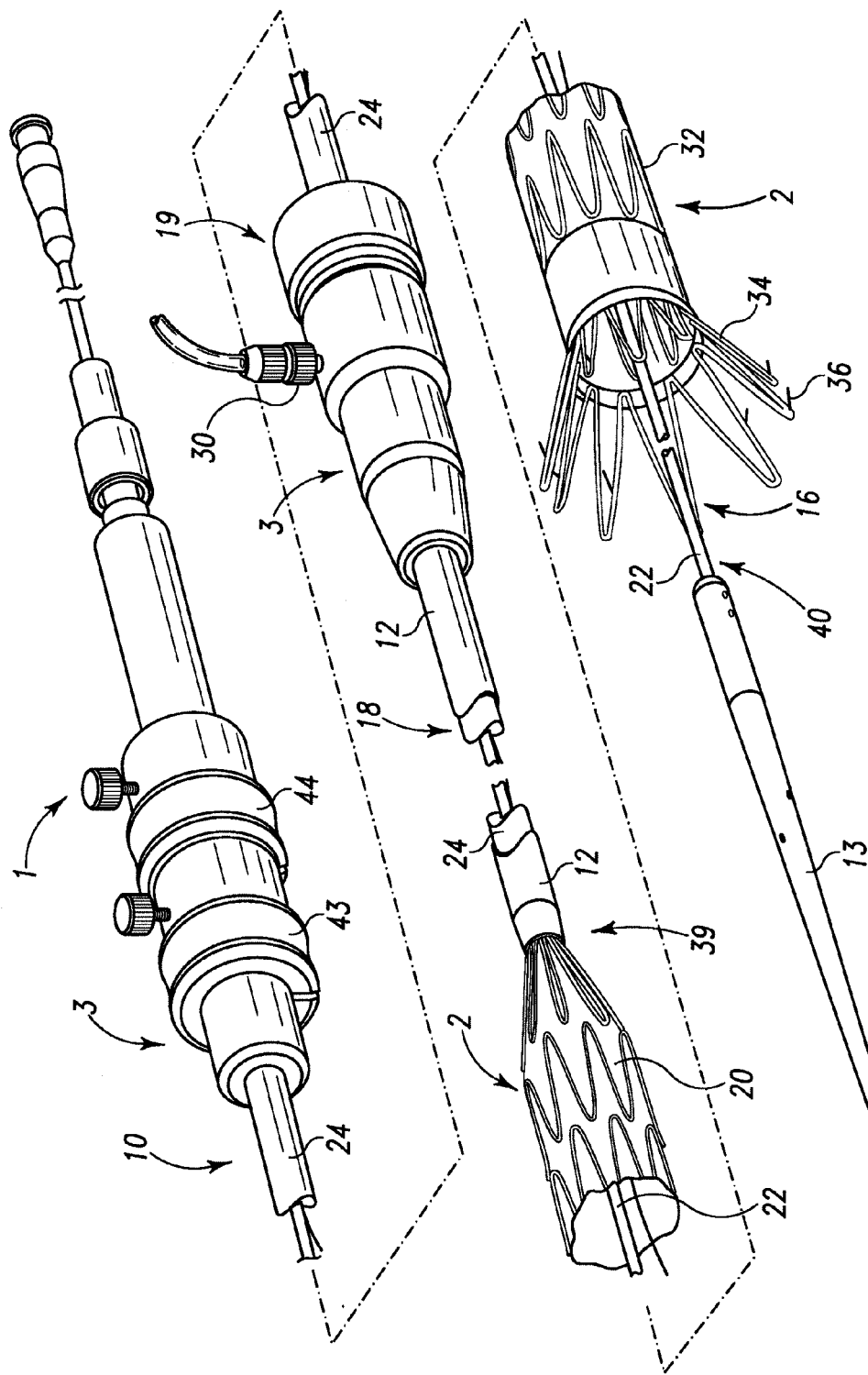
FIG. 3 is a perspective view of selected segments of a delivery and deployment device including a partially-deployed prosthesis.

FIGS. 1-3 show various exemplary devices 1 for delivering and deploying an expandable endoluminal prosthesis 20 in a body lumen. The device 1 comprises a prosthesis delivery section 2 and an external manipulation section 3. The delivery section 2 travels through the body lumen during the procedure and delivers the prosthesis to a desired deployment site. The external manipulation section 3 stays outside of the body during the procedure. The external manipulation section 3 can be manipulated by the operator to position and release or deploy the prosthesis 20 into the body lumen.

The delivery and deployment device 1 comprises a delivery catheter 10 and a sheath 12. The delivery catheter 10 and the sheath 12 are configured to selectively retain and release an expandable prosthesis 20. The delivery catheter 10 has a proximal end and a distal end. The distal end of the delivery catheter comprises a dilator head 13. The dilator head 13 is distally tapered to provide for atraumatic insertion into the body lumen (not shown). A guidewire lumen 15 extends longitudinally through the delivery catheter 10 between the proximal and distal ends. The delivery catheter 10 is configured to receive a guidewire 17 via the guidewire lumen 15 as shown in FIG. 1.

The delivery catheter 10 comprises a prosthesis receiving portion 16 and a prosthesis release portion 18, as shown in FIG. 2. The receiving portion 16 is disposed on a distal portion of the delivery catheter and is configured to receive the prosthesis 20 in a radially compressed configuration. As shown in FIGS. 2 and 3, the receiving portion 16 may comprise a catheter tube 22 having a longitudinally uniform external diameter D1.

The release portion 18 of the delivery catheter 10 is disposed generally proximally of the prosthesis 20. The release portion 18 can be manipulated, along with the sheath 12, to selectively deliver and deploy the prosthesis 20 in the body lumen. As shown in FIGS. 2 and 3, the release portion 18 may comprise a catheter tube 24 having a longitudinally uniform external diameter D2. Catheter tube 24 may have a diameter D2 that is greater than diameter D1. As shown in FIGS. 2 and 3, the release portion 18 includes a distal-facing annular abutment surface 23 at the transition between catheter tubes 22 and 24. The annular abutment surface 23 faces the proximal end of the prosthesis 20 and is configured to contact the proximal end of the prosthesis 20 during deployment, allowing the delivery catheter 10 to push the prosthesis 20 distally as the sheath 12 is pulled proximally in relation thereto. The delivery catheter 10 may comprise a single unitary structure as shown in FIG. 2. Alternately, the delivery catheter 10 may comprise a plurality of slidably interconnected catheters 22, 24 as shown in FIG. 3.

The sheath 12 comprises an elongate tubular body having a proximal and distal end and a sheath lumen 14. The sheath lumen 14 has a generally constant diameter between the proximal and distal ends. The sheath 12 extends proximally from the delivery section 2 to the user manipulation section 3. The delivery catheter 10 is slidably disposed within lumen 14. The sheath 12 releasably covers and retains the prosthesis 20 in a radially reduced configuration. The dilator head 13 and the sheath 20 preferably form a generally smooth transition so as to prevent trauma to the body lumen during delivery and deployment. The distal end of the sheath 12 travels within the body lumen during a procedure. The proximal end of the sheath 12 is configured to remain outside of the body during the procedure and can be directly manipulated by the operator to deploy the prosthesis 20.

Figure 4:
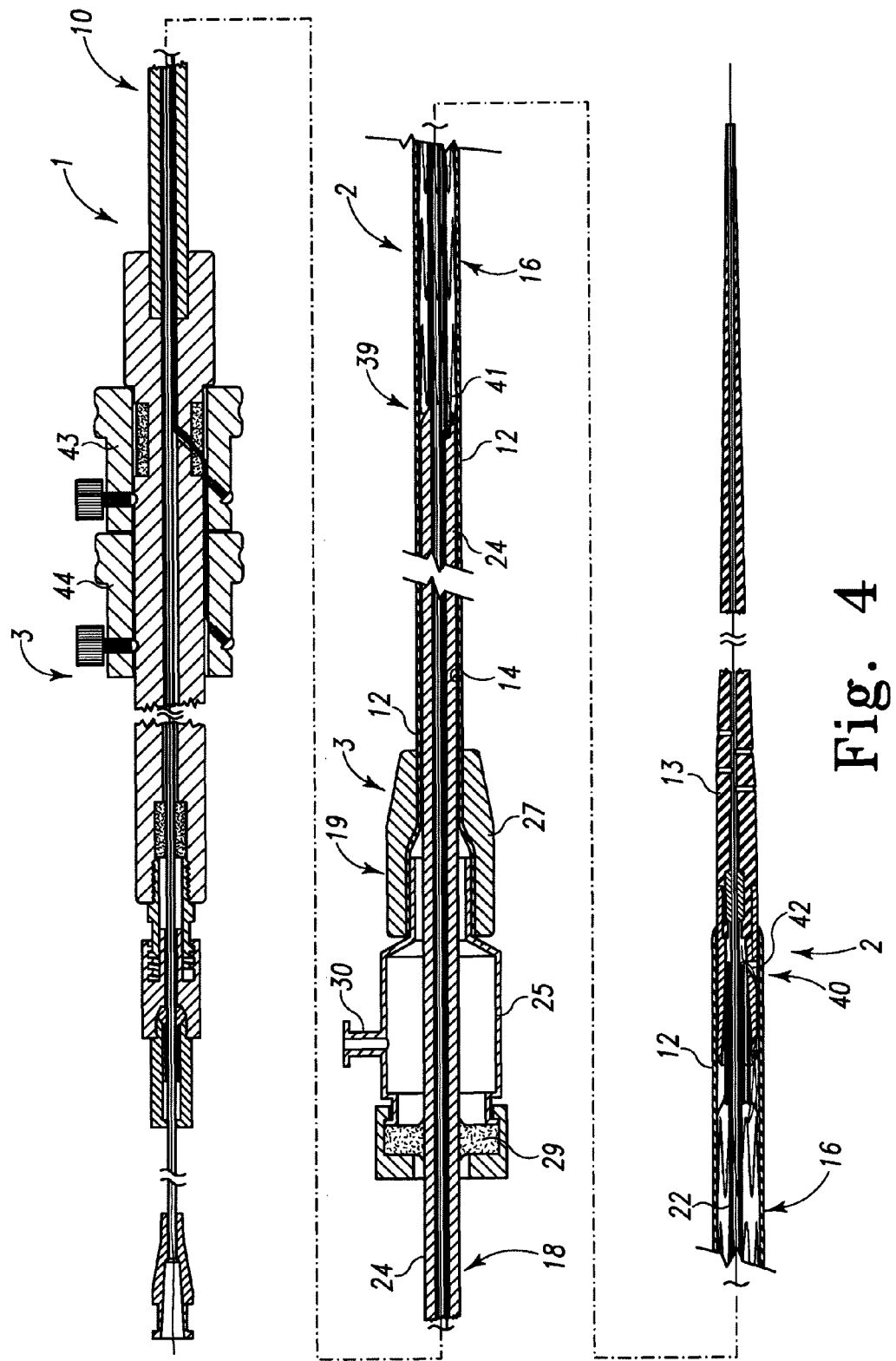
FIG. 4 is a cross-sectional view of the device of FIG. 3.

The sheath 12 may have a length, as shown in FIGS. 3 and 4, that is significantly greater than the length of the prosthesis 20. For example, the sheath 12 may have a length that is two or more times greater than the length of the prosthesis 20. Alternatively, the sheath 12 may have a length that is generally equal to or greater than the length of the prosthesis. The sheath 12 has a uniform internal diameter D3. The internal diameter D3 is generally equal to the external diameter D2 of catheter tube 24 so that the inner surface of the sheath 12 slidingly engages the delivery catheter 10.

The sheath may be made of any suitable biocompatible material, for example PTFE, nylon, or polyethylene. The sheath may optionally comprise a flat wire coil (not shown) to provide the sheath with additional flexibility and kink-resistance. U.S. Pat. No. 5,380,304 and U.S. Published Patent Application Number 2001/0034514 A1, incorporated herein by reference, propose various reinforced sheaths and methods of making the same that may be used in the present invention.

As shown in FIG. 3, the prosthesis 20 may comprise a stent graft having a plurality of self-expanding stents 32. The stents 32 cause the prosthesis 20 to expand during its release from the device 1. The stents 32 may cover and/or may be at least partially covered by a graft material. The prosthesis 20 also may include an exposed self-expanding zigzag stent 34 for anchoring the prosthesis 20 in the body lumen. The zigzag stent 34 may comprise barbs 36 that extend from the stent. When the zigzag stent 34 is released, the barbs 36 engage the surrounding lumen.

Various graft materials and configurations may be used in the present invention. Suitable graft configurations include, but are not limited to films, coatings, sheets of biocompatible fabrics, non-woven materials and porous materials. Examples of suitable graft materials include polyesters, such as poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments.

Stents used in the present invention may be self-expanding or balloon-expandable. A balloon-expandable stent or stent portion may be combined with a self-expanding stent or stent portion. Self-expanding stents can be made of stainless steel, materials with elastic memory properties, such as NITINOL, or any other suitable material. A suitable self-expanding stent includes Z-STENTS®, which are available from Cook, Incorporated, Bloomington, Ind. USA. Balloon-expandable stents may be made of various materials including, but not limited to, stainless steel (typically 316LSS, CoCr, Etc.).

The prosthesis 20 is retained in a radially reduced configuration between the delivery catheter 10 and the sheath 12. The sheath 12 is slidably disposed over the prosthesis 20 and the delivery catheter 10 in a proximal and a distal direction. The sheath 12 may be slid proximally with respect to the delivery catheter 10 and the prosthesis 20 to expose the prosthesis. To deploy the prosthesis 20, the operator slides the sheath 12 proximally while applying distal pressure to the delivery catheter 10 via catheter tube 24. Catheter tube 24 pushes the prosthesis 20 distally via the annular abutment surface 23 while the sheath 12 slides proximally in relation thereto. As the sheath 12 slides proximally, the catheter tube 24 pushes the prosthesis 20 distally from the receiving portion 16 and into the body lumen.

The delivery and deployment device 1 may further comprise a haemostatic sealing device 19 for controlling blood loss between the delivery catheter 10 and the sheath 12 during a procedure. FIGS. 3 and 4 illustrate an exemplary haemostatic sealing device 19. The device 19 includes a haemostatic seal 25 and a clamping collar 27 that clamps the sheath 12 to the haemostatic seal 25. The haemostatic seal 25 may include a seal ring 29 which may be made of silicone. The seal ring 29 engages the delivery catheter 10 and forms a tight haemostatic seal around catheter tube 24. The tight seal between the seal ring 29 and the catheter tube 24 creates an interference fit between the sealing device 19 and the delivery catheter 10, thereby increasing the sliding resistance between the sheath 12 and the catheter 10. The haemostatic sealing device 19 may also include a side tube 30 that facilitates the introduction of medical reagents between the delivery catheter 10 and the sheath 12.

The delivery and deployment device 1 may optionally include deployment control mechanisms 39, 40 as shown in FIGS. 3 and 4. Proximal control mechanism 39 releasably retains the proximal end of the prosthesis 20 and distal control mechanism 40 releasably retains the distal end of the prosthesis 20. Proximal control mechanism 39 may comprise a trigger wire 41 that releasably couples the proximal end of the prosthesis 20 to the delivery catheter 10. Likewise, the distal control mechanism 40 may comprise a trigger wire 42 that releasably couples the distal end of the prosthesis 20 to the delivery catheter 10. The trigger wires 41, 42 extend proximally to the external manipulation section 3 where they are coupled to trigger release devices 43, 44. Trigger release devices 43, 44 are configured to selectively decouple the proximal and distal ends of the prosthesis from the delivery catheter 10, respectively. Various prosthesis retention devices, configurations, and methods of use are disclosed in PCT Patent Publication Number WO 98/53761, previously incorporated by reference.

Figure 5:
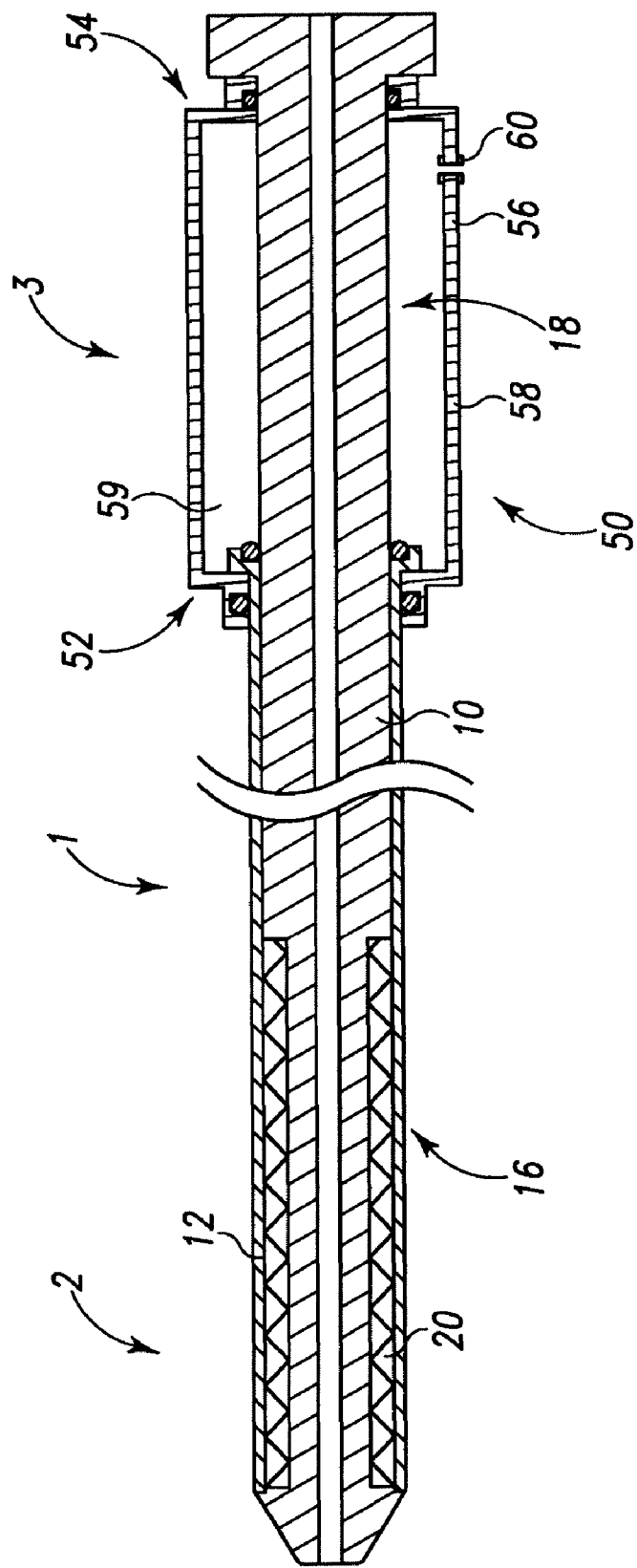
FIG. 5 is a cross-sectional view of a delivery and deployment device including an operating mechanism, according to an aspect of the invention.

FIG. 5 shows an exemplary system including a delivery catheter 10 and a sheath 12. A prosthesis 20 may be radially retained between the delivery catheter 10 and the sheath 12. To deploy the prosthesis 20, the sheath 12 is retracted proximally over the delivery catheter 10 to expose the prosthesis 20. According to an aspect of the present invention, an operating mechanism 50 may be provided to aid the operator in retracting the sheath 12 over the delivery catheter 10. The operating mechanism 50 is disposed in the user manipulation section 3 and may be disposed on the proximal end of the delivery catheter 10 as shown in FIG. 5. The operating mechanism 50 couples the sheath 12 to the delivery catheter 10 and is configured to pull the sheath 12 proximally with respect to the delivery catheter 10 and to push the delivery catheter 10 distally with respect to the sheath 12.

The operating mechanism 50 comprises a longitudinally contractible element 56. The contractible element 56 has an expanded length and a contracted length, where the expanded length is greater than the contracted length. A proximal end 54 of the contractible element 56 may be mechanically coupled to the delivery catheter 10 and a distal end 52 may be mechanically coupled to the sheath 12. When the contractible element 56 contracts, it pulls proximally on the sheath 12 and pushes distally on the delivery catheter 10. Contraction of the contractible element 56 causes the sheath 12 to slide proximally in relation to the delivery catheter 10 and the delivery catheter 10 to slide distally in relation to the sheath 12.

According to an aspect of the invention, the contractible element 56 may comprise a contractible air vessel 58. The air vessel 58 includes an air chamber 59 and has an expanded configuration and a contracted configuration. A proximal end 54 of the air vessel 58 is mechanically coupled to the delivery catheter 10 and a distal end 52 of the air vessel 58 is mechanically coupled to the sheath 12. The operating mechanism 50 further comprises a port 60. Port 60 is configured to provide pneumatic communication between an air pressure source (not shown) and the air chamber 59. To deploy the prosthesis 20, the operator causes the air vessel 58 to contract, for example by applying a sub-atmospheric pressure, or a vacuum to the air vessel 58 via port 60.

Figure 6:
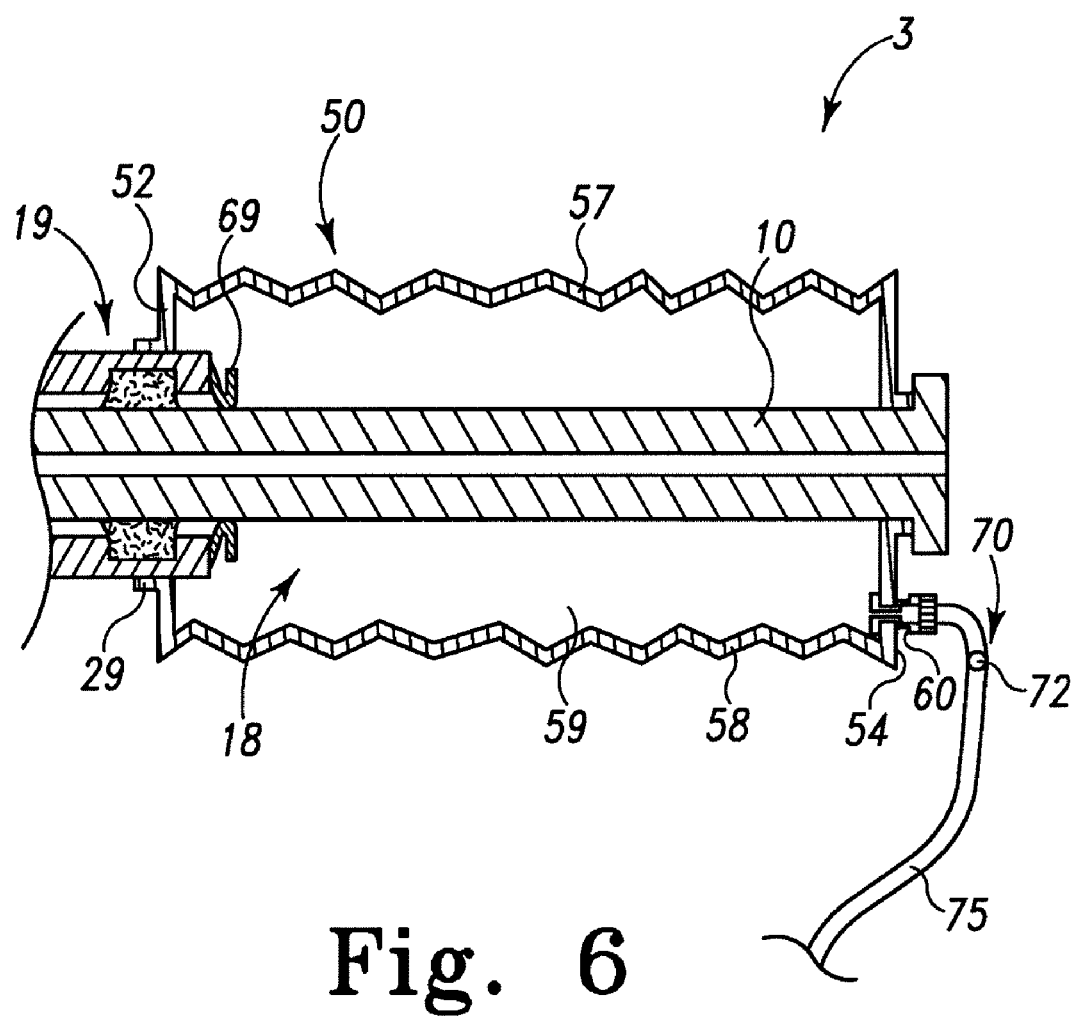
FIG. 6 is a cross-sectional view of an alternate delivery and deployment device including an operating mechanism, according to an aspect of the invention.

According to an aspect of the invention, the air vessel 58 may comprise a resilient tubular member 57, as shown in FIG. 6. The tubular member 57 may be made of a flexible plastic material, for example rubber, thermoplastic elastomer, polyolefin, or a fluoropolymer material including, but not limited to polytetrafluoroethylene and fluoroethylene-propylene. The proximal end 54 of the tubular member 57 is sealingly disposed about the delivery catheter 10. The distal end 52 of the tubular member 57 is sealingly disposed about the sheath 12. The tubular member 57 and the delivery and deployment device 1 define an annular air chamber 59.

As shown in FIG. 6, the distal end 52 of the tubular member 57 may be coupled to the sheath 12 via the haemostatic sealing device 19. A pneumatic seal 69, for example a v-ring seal, may be provided to seal the interface between the air chamber 59 and the haemostatic sealing device 19. The operating mechanism 50 further comprises a port 60 that is configured to provide pneumatic communication between a vacuum pressure source (not shown) and the air chamber 59. The port 60 may include a connector, for example a female luer for providing a connection with an air pressure source.

According to an aspect of the invention, the air vessel 58 may comprise a bellows. The bellows preferably has a generally circular transverse cross-section, but alternately may have a non-circular transverse cross-section, for example a polygonal cross-section. As used herein, the term "bellows" shall mean a flexible contractible and/or expansible vessel, which may include, but does not require a pleated structure. A proximal end 54 of the bellows is mechanically coupled to the delivery catheter 10 and a distal end 52 is mechanically coupled to the sheath 12. The bellows may be constructed of any suitable material, for example metal, rubber, thermoplastic elastomer, polyolefin, or a fluoropolymer material including, but not limited to polytetrafluoroethylene and fluoroethylene-propylene.

The bellows has an exterior diameter and a wall thickness that will be selected according to the particular force requirements of the system. In general, the force exerted by the bellows will be proportional to the area of the inner, distal end of the bellows. An exemplary tubular bellows may comprise an exterior diameter between 1 inch and 3 inches. Alternately, the bellows may comprise an exterior diameter between 1.3 inches and 1.8 inches. An exemplary bellows may have a wall thickness of approximately 0.025 inches. The diameter and wall thickness may be greater or less depending on the particular requirements of the system.

According to another aspect of the invention, the operating mechanism 50 may comprise an actuation switch 70. The actuation switch 70 is used to control the manner of deployment and is configured to selectively commence and halt contraction of the contractible element. In FIG. 6, the operating mechanism 50 comprises a switch 70 that includes a reversibly sealable aperture 72 formed in the air line 75 between the port 60 and the air source. When the switch 70 is closed, for example where the aperture 72 is occluded, the air vessel may be pressurized via port 60. When the switch 70 is open, the aperture 72 prevents pneumatic communication between the air source and the air chamber 59, thereby preventing the vessel 58 from contracting. During deployment, while the air vessel 58 is contracting, the switch 70 may be opened, relieving pressure in the air chamber 59 and causing an immediate halt in the retraction of the sheath 12.

In some embodiments, a check valve may be provided in series with the port 60. Such a valve is preferable to prevent a compressed air vessel, for example a polymer bellows, from expanding when pneumatic communication is disrupted between the air source and the air chamber 59 (e.g., when the vacuum is turned off or when the switch 70 is opened).

Figure 7:
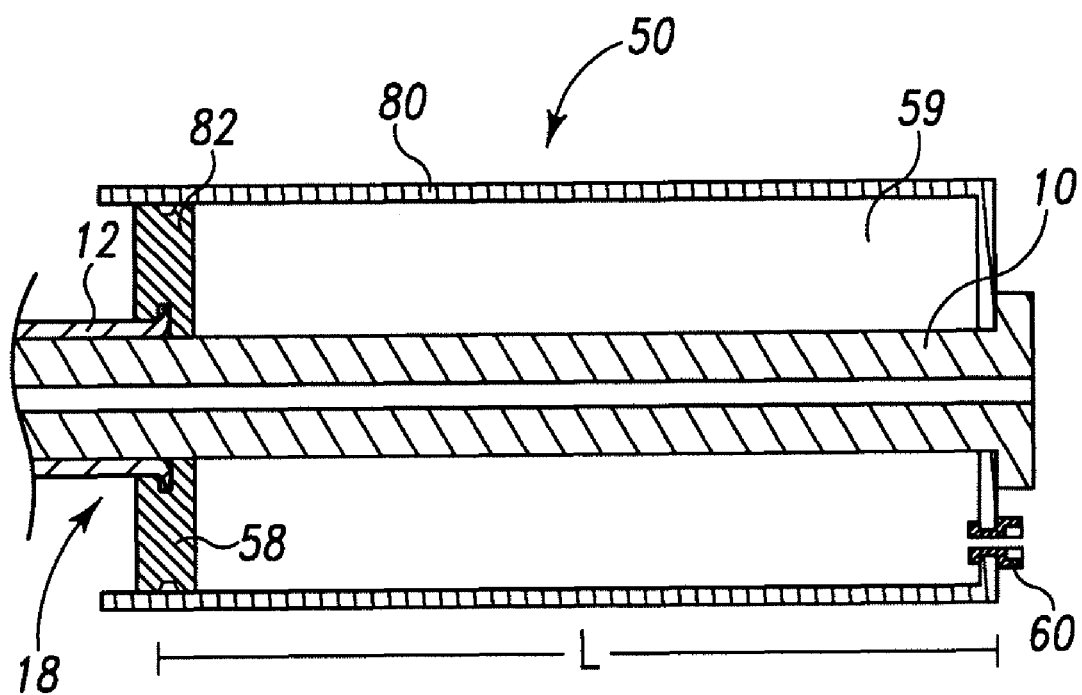
FIG. 7 is a cross-sectional view of an alternate delivery and deployment device including an operating mechanism, according to an aspect of the invention.

FIG. 7 shows another operating mechanism 50 according to an aspect of the invention. The operating mechanism 50 comprises a cylinder 80 and a piston 82. Cylinder 80 and piston 82 form a contractible air vessel 58 defining an air chamber 59. The operating mechanism 50 comprises a port 60 for providing pneumatic communication between a pressure source (not shown) and the air chamber 59. The piston 82 is mechanically coupled to the sheath 12. The cylinder 80 is mechanically coupled to the delivery catheter 10. To actuate the operating mechanism 50, a vacuum may be drawn on the air chamber 59, causing the piston 82 to slide proximally in the cylinder 80. The piston 82 pulls the sheath 12 proximally with respect to the delivery catheter 10 and the cylinder 80 pushes the delivery catheter 10 distally with respect to the sheath 12.

The contractible vessel 58 causes the sheath 12 to retract over the delivery catheter 10 a maximum distance that is generally proportional to the difference between the expanded length and the contracted length of the vessel. For example, a bellows having a 10 inch expanded length and a 2 inch contracted length will be sufficient to retract sheath 12 over a distance of approximately 8 inches. In the embodiments previously shown, the ratio between sheath retraction distance and vessel contraction distance is approximately 1 to 1.

Figure 8:
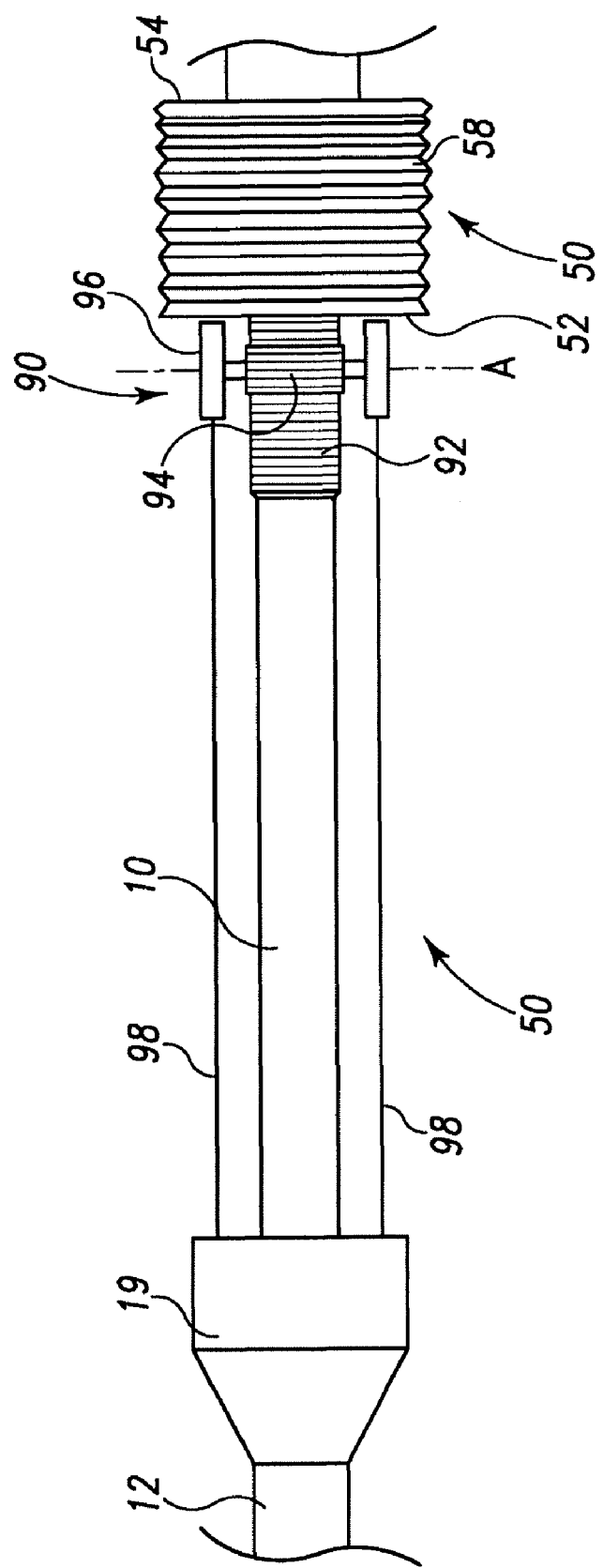
FIG. 8 is a side elevational view of an operating mechanism including a mechanical conversion mechanism according to an aspect of the invention.

FIG. 8 illustrates another operating mechanism 50 according to an aspect of the present invention. The operating mechanism 50 comprises a contractible air vessel 58, for example a bellows. A proximal end 54 of the bellows is mechanically coupled to the delivery catheter 10 and a distal end 52 of the bellows is mechanically coupled to the sheath 12. The operating mechanism 50 further comprises a conversion mechanism 90 disposed between the bellows and the sheath 12. The conversion mechanism 90 is configured to convert vessel contraction into sheath retraction.

The conversion mechanism 90 may include a linear gear 92 and a pinion 94. The linear gear 92 is connected to the bellows such that contraction and expansion of the bellows causes the linear gear 92 to slide proximally and distally, respectively. The linear gear 92 drives the pinion 94, which is operably connected to a pulley 96. The pulley 96 drives a retractable cable 98 that is connected to the sheath. In FIG. 8, the cable 98 is connected to the sheath 12 via the haemostatic sealing device 19. In operation, as the bellows contracts, the linear gear 92 slides proximally, causing the pinion 94 to rotate about axis A. As pinion 94 rotates, it drives pulley 96, causing the pulley to rotate about axis A. As the pulley 96 rotates, it retracts the cable 98, thereby pulling the sheath proximally.

The conversion mechanism 90 converts vessel contraction into sheath retraction. In the embodiment shown, the radii of the pulley and the pinion can be varied to affect the ratio between sheath retraction and vessel contraction. In general, as the radius of the pulley increases with respect to the radius of the pinion, the ratio will increase. Conversely, as the radius of the pulley decreases with respect to the radius of the pinion, the ratio will decrease. Accordingly, the conversion mechanism 90 may provide a ratio that is less than or equal to 1 or a ratio that is greater than or equal to 1.

A ratio of greater than 1 will be desirable where the air vessel has a maximum vessel contraction distance that is less than the required sheath retraction distance. In an exemplary embodiment, the operating mechanism 50 in FIG. 8 may be provided with a bellows having an expanded length of 2 inches that is configured to contract over a distance of approximately 1.2 inches. The gear ratio between pinion 94 and linear gear 92 is configured so that pinion 94 revolves approximately 1.7 times about axis A during the contraction of the bellows, causing the pulley 96 to revolve approximately 1.7 times about axis A. If the pulley 96 has a diameter of approximately 1.5 inches, the system will retract the cable 98, and thus the sheath 12 over a distance of approximately 8 inches, based on a vessel contraction of 1.2 inches. In a preferred embodiment, the conversion mechanism provides a ratio that is greater than 2 to 1, and more preferably greater than 4 to 1.

On the other hand, a ratio of less than 1 may be desirable where the maximum force provided by the air vessel is less than the force normally required to retract the sheath. By adjusting the gear ratios in the example above, the conversion mechanism may be configured to decrease the effort required to retract the sheath, while correspondingly increasing the required air vessel contraction distance. In general, the selection of appropriate gears and gear ratios to provide a particular mechanical advantage will be readily understood by one of ordinary skill in the art. In an exemplary embodiment, the conversion mechanism provides a ratio of less than 0.8 to 1, less than 0.5 to 1, or less than 0.2 to 1.

Figure 9A:
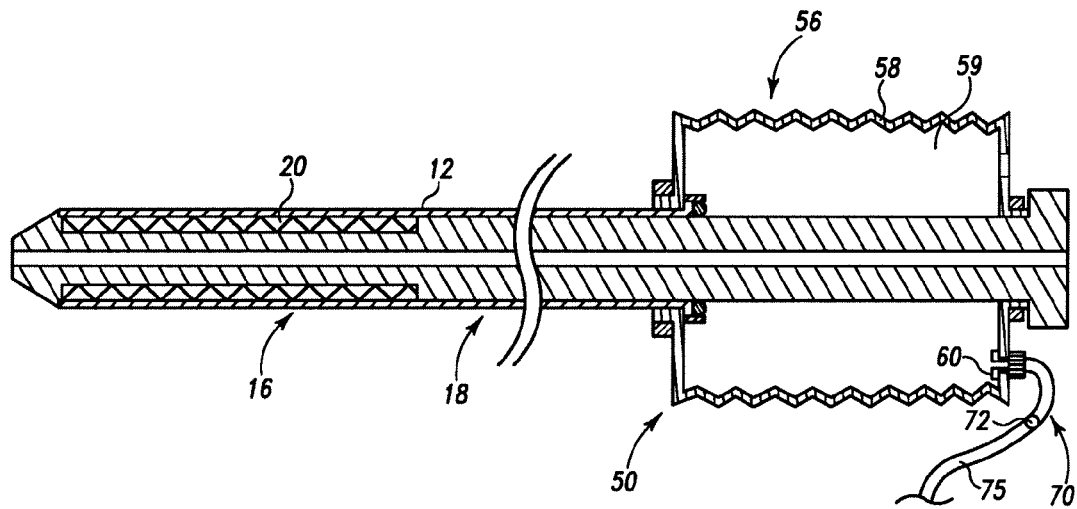
FIG. 9A is a cross-sectional view of a delivery and deployment device in a pre-deployment state.
Figure 9B:
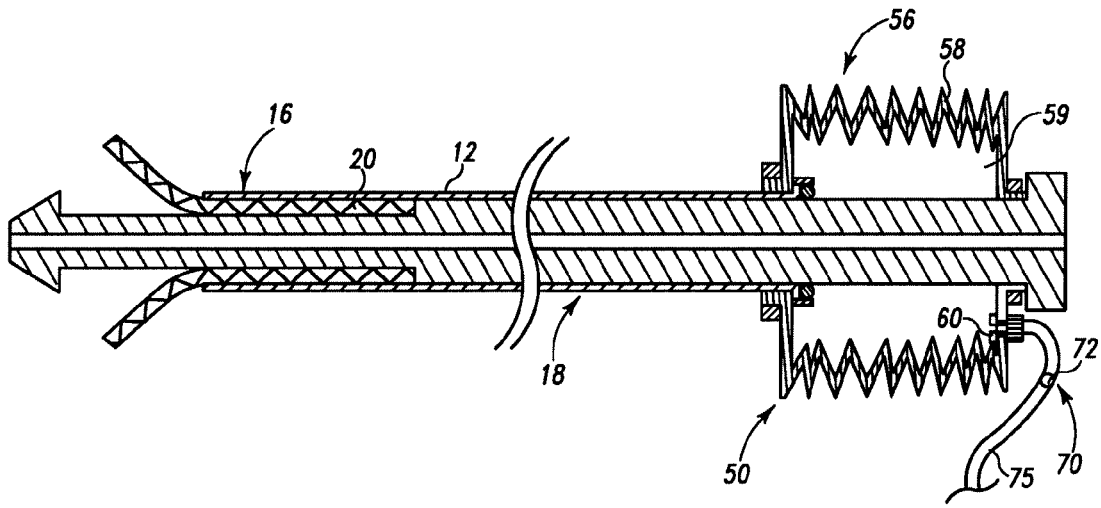
FIG. 9B is a cross-sectional view of a delivery and deployment device in a partially-deployed state.

A method of deploying a prosthesis 20 into a body lumen will now be described with reference to FIGS. 9A-9C. First, a guidewire 17 is introduced into the body lumen and advanced until the tip is beyond the region into which the prosthesis 20 is to be deployed. The delivery and deployment device 1 is then inserted into the body lumen over the guide wire 17 (as shown in FIG. 1) and positioned in the treatment area by radiographic techniques that are generally known in the art. At this stage, the prosthesis 20 is fully retained in the delivery and deployment device 1 in a radially-constrained configuration by the sheath 12 as shown in FIG. 9A.

Once the prosthesis 20 is properly positioned, the device 1 is ready for deployment. To deploy the prosthesis 20, the operator may use an operating mechanism 50. FIGS. 9A-9C illustrate deployment using a bellows operating mechanism 50 as described above. It should be understood that the operating mechanism 50 could include any contractible element 56 within the scope of the present invention. Additionally, the operating mechanism 50 could comprise a mechanical conversion mechanism 90 for converting vessel contraction into sheath retraction.

The operating mechanism 50 is connected to a sub-atmospheric, or air vacuum pressure source (not shown) through port 60 via air line 75. The pressure source causes the bellows to contract. As the bellows contracts, it pulls the sheath 12 proximally over the delivery catheter 10 and the prosthesis 20. As the sheath 12 retracts, the prosthesis 20 becomes exposed and is thereby allowed to expand into the body lumen, as shown in FIG. 9B. In order to maintain proper prosthesis 20 positioning in the body lumen, the delivery catheter 10 is held steady relative to the sheath 12 during deployment. The operator may manually fix the position of the delivery catheter 10. Alternately, a delivery fixture (not shown) may be provided to hold the delivery catheter 10 steady during deployment.

The operator may control the manner of deployment by varying the input from the pressure source during the procedure. To this end, the operator may manually adjust the pressure from the source. Additionally, the operating mechanism 50 may comprise an actuation switch 70. To initiate retraction, the operator covers aperture 72, thereby allowing pneumatic communication between the pressure source and the air chamber 59. To halt retraction, the operator uncovers aperture 72, thereby cutting off pneumatic communication between the pressure source and the air chamber 59.

Figure 9C:
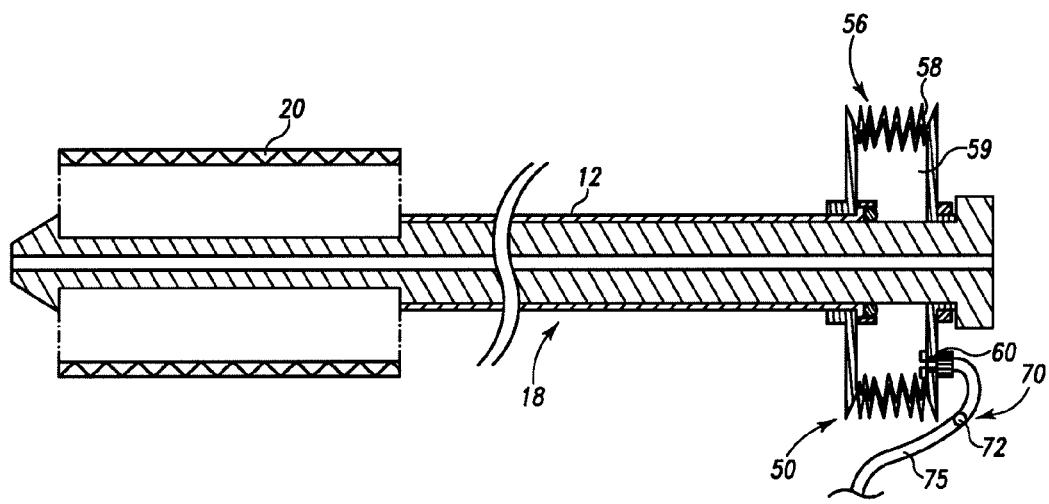
FIG. 9C is a cross-sectional view of a delivery and deployment device in a fully-deployed state.

FIG. 9C shows the delivery and deployment device in a fully deployed state. The bellows is in a contracted configuration, the sheath 12 is completely retracted from the prosthesis 20, and the prosthesis 20 is expanded within the body lumen. The delivery and deployment device and the guide wire may now be removed from the body lumen.

Throughout this specification various indications have been given as to preferred and alternative embodiments of the invention. However, it should be understood that the invention is not limited to any one of these. It is therefore intended that the foregoing detailed description be regarded as illustrative rather than limiting, and that it be understood that it is the appended claims, including all equivalents, that are intended to define the spirit and scope of this invention.

What is claimed is:

1. A system for delivering and deploying an expandable endoluminal prosthesis, the system comprising:
   a distal end portion defining a prosthesis delivery section and a proximal end portion defining an external manipulation section;
   an elongate sheath having a proximal end disposed at the proximal end portion of the system, a distal end disposed at the distal end portion of the system, and an inner lumen;
   a delivery catheter having a proximal end disposed at the proximal end portion of the system and a distal end disposed at the distal end portion of the system, wherein the delivery catheter is slidably disposed within the sheath lumen; and
   an operating mechanism comprising a contractible air vessel disposed entirely at the external manipulation section and having an expanded length and a contracted length, the air vessel coupling the sheath and the delivery catheter, so that pneumatic contraction of the air vessel causes the sheath to retract proximally over the delivery catheter,
   wherein the air vessel comprises a resilient tubular member having a proximal end, a distal end, and a lumen disposed therebetween, the tubular member being radially disposed about the sheath and the delivery catheter, the distal end of the tubular member sealingly engaging the sheath and the proximal end of the tubular member sealingly engaging the delivery catheter, whereby the tubular member, the sheath, and the delivery catheter define an annular air chamber therebetween.

2. The system according to claim 1, wherein the air vessel comprises a tubular bellows.

3. The system according to claim 1, wherein the operating mechanism comprises an air port configured to provide pneumatic communication between the air vessel and a pressure source.

4. The system according to claim 3, wherein the operating mechanism comprises an actuation switch configured to selectively halt contraction of the air vessel by effecting pneumatic communication between the pressure source and the air vessel.

5. The system according to claim 1, wherein the operating mechanism comprises a check valve for preventing expansion of the air vessel.

6. The system according to claim 1, wherein the operating mechanism comprises a mechanical conversion mechanism for converting a vessel contraction into a sheath retraction.

7. The system according to claim 6, wherein the conversion mechanism comprises a linear gear configured to mechanically increase sheath retraction in relation to vessel contraction.

8. The system according to claim 6, wherein the ratio between sheath retraction and vessel contraction is greater than 1.

9. The system according to claim 1, wherein the air vessel is vacuum-contractible.

10. A system for delivering and deploying an expandable endoluminal prosthesis, the system comprising:
   a distal end portion defining a prosthesis delivery section and a proximal end portion defining an external manipulation section;
   an elongate sheath having a proximal end disposed at the proximal end portion of the system, a distal end disposed at the distal end portion of the system, and an inner lumen;
   a delivery catheter having a proximal end disposed at the proximal end portion of the system and a distal end disposed at the distal end portion of the system, wherein the delivery catheter is slidably disposed within the sheath lumen; and
   an operating mechanism comprising a contractible air vessel disposed entirely at the external manipulation section and having an expanded length and a contracted length, the air vessel coupling the sheath and the delivery catheter, so that pneumatic contraction of the air vessel causes the sheath to retract proximally over the delivery catheter, wherein the air vessel comprises a tubular bellows having a proximal end, a distal end, and a lumen disposed therebetween, the bellows being radially disposed about the sheath and the delivery catheter, the distal end of the bellows sealingly engaging the sheath and the proximal end of the bellows sealingly engaging the delivery catheter, whereby the bellows, the sheath, and the delivery catheter define an annular air chamber therebetween, and wherein the system further comprises:

an air port configured to provide pneumatic communication between the air vessel and a pressure source;

an actuation switch configured to selectively halt contraction of the air vessel by effecting pneumatic communication between the pressure source and the air vessel;

a check valve for preventing expansion of the air vessel;

a mechanical conversion mechanism for converting a vessel contraction into a sheath retraction, the conversion mechanism comprising a linear gear configured to mechanically increase sheath retraction in relation to vessel contraction so that the ratio between sheath retraction and vessel contraction is greater than 1; and wherein the air vessel is vacuum-contractible.

11. A pneumatic operating mechanism for an endoluminal prosthesis delivery and deployment device having a distal end portion defining a prosthesis delivery section and a proximal end portion defining an external manipulation section, the device having a sheath and a delivery catheter slidingly disposed within a lumen of the sheath, the operating mechanism comprising:

a contractible air vessel disposed entirely at the external manipulation section and having a proximal end, a distal end, an expanded length, and a contracted length;

wherein the proximal end of the air vessel is engageable with the delivery catheter and the distal end of the air vessel is engageable with the sheath so that contraction of the air vessel causes the sheath to retract proximally over the delivery catheter, wherein the air vessel comprises a resilient tubular member having a proximal end, a distal end, and a lumen disposed therebetween, the tubular member being radially disposed about the sheath and the delivery catheter, the distal end of the tubular member sealingly engaging the sheath and the proximal end of the tubular member sealingly engaging the delivery catheter, whereby the tubular member, the sheath, and the delivery catheter define an annular air chamber therebetween.

12. The operating mechanism according to claim 11, wherein the air vessel comprises a tubular bellows.

13. The operating mechanism according to claim 11, further comprising a check valve for preventing expansion of the air vessel.

14. The operating mechanism according to claim 11, further comprising an air port configured to provide pneumatic communication between the air vessel and a pressure source.

15. The operating mechanism according to claim 11, further comprising a mechanical conversion mechanism for converting a vessel contraction into a sheath retraction, the conversion mechanism including a linear gear configured to mechanically increase or decrease sheath retraction in relation to vessel contraction.

16. The operating mechanism according to claim 15, wherein the ratio between sheath retraction and vessel contraction is greater than 1.

17. The operating mechanism according to claim 11, wherein the air vessel comprises a tubular bellows, the operating mechanism further comprising:

a check valve for preventing expansion of the air vessel;

an air port configured to provide pneumatic communication between the air vessel and a pressure source; and a mechanical conversion mechanism for converting a vessel contraction into a sheath retraction, the conversion mechanism including a linear gear configured to mechanically increase or decrease sheath retraction in relation to vessel contraction, wherein the ratio between sheath retraction and vessel contraction is greater than 1.

18. A method of deploying an expandable endoluminal prosthesis, the method comprising the steps of:

providing a prosthesis delivery and deployment system having a distal end portion defining a prosthesis delivery section and a proximal end portion defining an external manipulation section, the system comprising an elongate sheath having a proximal end, a distal end, and an inner lumen and a delivery catheter having a proximal end and a distal end, wherein the delivery catheter is slidably disposed within the sheath lumen;

providing an operating mechanism comprising a contractible air vessel disposed entirely at the external manipulation section and having an expanded length and a contracted length, wherein the air vessel couples the sheath and the delivery catheter; and pneumatically contracting the air vessel to cause the sheath to retract over the delivery catheter, and wherein the air vessel comprises a resilient tubular member having a proximal end, a distal end, and a lumen disposed therebetween, the tubular member being radially disposed about the sheath and the delivery catheter, the distal end of the tubular member sealingly engaging the sheath and the proximal end of the tubular member sealingly engaging the delivery catheter, whereby the tubular member, the sheath, and the delivery catheter define an annular air chamber therebetween.

19. The method according to claim 18, wherein the contracting step comprises applying vacuum pressure to the air vessel.

20. A system for delivering and deploying an expandable endoluminal prosthesis, the system comprising:

an elongate sheath having a proximal end, a distal end, and an inner lumen;

a delivery catheter having a proximal end and a distal end, wherein the delivery catheter is slidably disposed within the sheath lumen; and an operating mechanism comprising a contractible air vessel having an expanded length and a contracted length, the air vessel coupling the sheath and the delivery catheter, so that pneumatic contraction of the air vessel causes the sheath to retract proximally over the delivery catheter;

where the air vessel comprises a resilient tubular member having a proximal end, a distal end, and a lumen disposed therebetween, the tubular member being radially disposed about the sheath and the delivery catheter, the distal end of the tubular member sealingly engaging the sheath and the proximal end of the tubular member sealingly engaging the delivery catheter, whereby the tubular member, the sheath, and the delivery catheter define an annular air chamber therebetween.

* * * * *